(12) United States Patent
Shiber

(10) Patent No.: US 6,767,353 B1
(45) Date of Patent: Jul. 27, 2004

(54) THROMBECTOMY CATHETER

(76) Inventor: Samuel Shiber, 365 Kearney Cir., Manchester, NH (US) 03104

( * ) Notice: Subject to any disclaimer, the term of this patent is extended or adjusted under 35 U.S.C. 154(b) by 179 days.

(21) Appl. No.: 10/086,465

(22) Filed: Mar. 1, 2002

(51) Int. Cl.$^7$ ............................. A61B 17/22; A61D 1/02
(52) U.S. Cl. ..................................................... 606/159
(58) Field of Search ................................ 606/159, 181, 606/191–198, 108, 170; 604/35, 22, 27–28, 30, 96, 101, 264, 280

(56) References Cited

U.S. PATENT DOCUMENTS

| | | |
|---|---|---|
| 3,352,303 A | 11/1967 | Delaney |
| 3,565,062 A | 2/1971 | Kuris |
| 3,614,953 A | 10/1971 | Moss |
| 4,037,599 A | 7/1977 | Raulerson |
| 4,445,509 A | 5/1984 | Auth |
| 4,468,216 A | 8/1984 | Muto |
| 4,631,052 A | 12/1986 | Kensey |
| 4,646,736 A | 3/1987 | Auth |
| 4,669,469 A | 6/1987 | Gifford, III |
| 4,692,139 A | 9/1987 | Stiles |
| 4,696,667 A | 9/1987 | Masch |
| 4,728,319 A | 3/1988 | Masch |
| 4,729,763 A | 3/1988 | Henrie |
| 4,735,604 A | 4/1988 | Watmough |
| 4,749,376 A | 6/1988 | Kensey |
| 4,790,812 A | 12/1988 | Hawkins, Jr. |
| 4,808,153 A | 2/1989 | Parisi |
| 4,870,953 A | 10/1989 | DonMichael |
| 4,894,051 A | 1/1990 | Shiber |
| 4,950,257 A | 8/1990 | Hibbs |
| 4,968,307 A | 11/1990 | Dake |
| 4,976,690 A | 12/1990 | Solar |
| 4,990,134 A | 2/1991 | Auth |
| 5,011,488 A | 4/1991 | Ginsburg |
| 5,058,570 A | 10/1991 | Idemoto |
| 5,084,013 A | 1/1992 | Takase |
| 5,163,905 A | 11/1992 | DonMichael |
| 5,176,693 A | 1/1993 | Pannek, Jr. |
| 5,181,920 A | 1/1993 | Mueller |
| 5,248,296 A | 9/1993 | Alliger |
| 5,273,526 A | * 12/1993 | Dance et al. .................. 604/35 |
| 5,370,609 A | 12/1994 | Drasler |
| 5,419,774 A | 5/1995 | Willard |
| 5,423,799 A | 6/1995 | Shiu |
| 5,437,632 A | 8/1995 | Engelson |
| 5,451,233 A | 9/1995 | Yock |
| 5,476,450 A | 12/1995 | Ruggio |
| 5,484,424 A | 1/1996 | Cottenceau |
| 5,490,859 A | 2/1996 | Mische |
| 5,527,292 A | 6/1996 | Adams |
| 5,683,640 A | 11/1997 | Miller |
| 5,688,234 A | 11/1997 | Frisbie |
| 5,695,507 A | 12/1997 | Auth |
| 5,713,848 A | 2/1998 | Dubrul |
| 5,749,849 A | 5/1998 | Engelson |
| 5,766,191 A | 6/1998 | Trerotola |
| 5,827,229 A | 10/1998 | Auth |
| 5,851,171 A | 12/1998 | Gasson |

(List continued on next page.)

Primary Examiner—Vy Bui
(74) Attorney, Agent, or Firm—Samuel Shiber

(57) ABSTRACT

A flexible catheter having a guidewire lumen extending throughout its length and a distal section that is insertable, over the guidewire, into a patient's vasculature for removing obstructive material, comprising an inner tube nested in an outer tube with an unobstructed void defined between them that is connectable to negative pressure, the inner tube is preferably rotatable by a motor for reducing the frictional resistance to the sliding of the inner tube over the guidewire as well as for reducing the frictional resistance to the movement of obstructive material through the void, the distal section of the catheter consists essentially of the distal portions of the tubes, wherein the inner tube has no connection to any element for cutting or fragmenting the obstructive material thereby reducing the likelihood of dislodging the material prior to aspirating it into the void.

4 Claims, 4 Drawing Sheets

U.S. PATENT DOCUMENTS

| | | | |
|---|---|---|---|
| 5,897,567 A | 4/1999 | Ressemann | |
| 5,938,645 A | 8/1999 | Gordon | |
| 6,001,112 A | 12/1999 | Taylor | |
| 6,113,614 A * | 9/2000 | Mears | 606/159 |
| 6,206,898 B1 | 3/2001 | Honeycutt | |
| 6,287,271 B1 | 9/2001 | Dubrul | |
| 6,290,689 B1 | 9/2001 | Delaney | |

* cited by examiner

THROMBECTOMY CATHETER

BACKGROUND OF THE INVENTION

Occlusive diseases of the vasculature are a leading cause of mortality and morbidity. While the nature of vascular diseases vary greatly, the underlying clinical cause is basically a reduction in blood flow due to an accumulation of obstructive material in the vessels feeding (arteries) or draining (veins) the affected organ. The obstructive material varies in hardness and composition. Harder obstructive material often contain calcified atherosclerotic plaque whereas softer material often contains blood clots (thrombus) and the disease is commonly caused by a combination of the two.

When such obstructions develop abruptly in the coronary vessels (feeding the heart), a heart attack occurs and in the brain it is referred to as a stroke. When obstructions develop over a longer period in the coronary vessels patients experience angina; while in the legs, they may suffer from pain ulcers and gangrene.

Clinical treatment of a vascular disease may involve surgical, pharmaceutical, or catheter based therapies. The choice of treatment depends on many factors, including the extent and location of disease and the nature of the obstruction. Surgical methods for treating vascular occlusive disease tend to be highly invasive and are typically associated with longer hospital stays and higher costs. Pharmaceutical treatment with thrombus dissolving drugs takes time to work, may inadvertently cause bleeding elsewhere in the body and may also dislodge large particles of obstructive material which is undesirable. Catheter-based therapies use various mechanisms to fragment, displace or remove vascular obstructions, and when such catheters are used percutaneously they offer shortened procedure times and reduced hospital stays.

Various designs of catheters have been developed for removing harder obstructive material from the vasculature.

For example, U.S. Pat. No. 4,669,469 (Gifford) shows a catheter with a distal cylindrical housing with a side window that excises the obstructive material with a rotating blade disposed in the housing. However, the rigidity of the housing limits the utility of the device in tortuous vessels such as coronary arteries so that in the process of advancing such a rigid device past the material to bring the side window into position, it may dislodge some of the obstructive material down stream.

Another example is U.S. Pat. No. 4,990,134 (Auth) which shows an abrading device carried at the distal end of a flexible drive shaft. The device uses a high speed abrasive burr that pulverizes hard atherosclerotic but is less effective in dealing with soft tissue like material which may be dislodged into the blood and travel downstream.

Other designs of catheters have been developed for removing softer obstructive material from the vasculature.

For example, U.S. Pat. No. 6,287,271 (Dubrul) shows a combination of rotational and longitudinal vibrations together with an injection of a lysing agent to break up the obstructive material in the vessels with an optional aspiration channel that is located proximally at a distance from the area where the tip fragments the material. Thus, once the obstructive material is fragmented some of the fragments may flow with the blood downstream.

Another example is U.S. Pat. No. 5,476,450 (Ruggio) and U.S. Pat. No. 5,938,645 (Gordon) that show an asymmetrically partitioned lumen whose cross-sectional moment of inertia is higher in certain direction. This asymmetry together with the off-center position of the guidewire, makes it harder for the catheter to turn while advancing along a three dimensional path that is commonly encountered in the vasculature of the heart and elsewhere.

SUMMARY OF THE INVENTION

The present invention generally relates to medical devices and, more particularly, to a catheter for removing soft obstructive material such as thrombus from a patient's vasculature.

In accordance with one aspect of the present invention, a flexible catheter is provided having a guidewire lumen extending throughout its length and a distal section that is insertable, over a guidewire, into a patient's vasculature for removing an obstructive material. The catheter comprises a guidewire shield in the form of an inner tube nested in an outer tube with an unobstructed void defined between them that is connectable to negative pressure.

The inner tube is preferably rotated by a motor to reduce the frictional resistance to the sliding of the inner tube over the guidewire as well as for reducing the frictional resistance to the movement of obstructive material through the void. The direction of the rotation of the inner tube is reversible to avoid wrapping-up blood fibers around the inner tube, thus avoiding the creation of a new very resilient obstruction on the inner tube. Additionally, the inner tube may have a non-circular cross section to agitate the obstructive material that is passing through the void and prevent the material from organizing to form an obstruction therein. To enhance the flexibility of the distal portion of the catheter a wall thickness of the inner tube can be reduced, gradually or in steps, since the torque that the inner tube has to carry lessens towards the distal end.

The distal section of the catheter consists essentially of the distal portions of the tubes which are made preferably from an flexible biocompatible plastic material minimizing the mechanical trauma to the vasculature. The inner tube has no connection to any element for cutting or fragmenting the obstructive material so as not to disturb the obstructive material while it is still in the vasculature, prior to being aspirated into the void, thereby reducing the danger of releasing material fragments into the blood stream. Thus, the only effect of the rotation of the inner tube on the material is to minimize the resistance to movement of the material that already has been aspirated into the void in response to the negative pressure that prevails in the void.

In accordance with another aspect of the present invention, a method of removing obstructive material from a vasculature is provided, comprising several steps:

Introducing a guidewire, through a patient's vasculature to the vicinity of the obstructive material.

Inserting into the vasculature, over the guidewire, a distal section of a catheter, with an inner tube nested in an outer tube, to the vicinity of the obstructive material while selectively rotating the inner tube as needed to reduce the frictional resistance to movement of the catheter over the guidewire.

Creating negative pressure in a void that is defined between the tubes.

Selectively rotating the inner tube as needed to reduce the frictional resistance to movement of the material and to optionally agitate the material that is already in the void.

Withdrawing the catheter from the patient.

DETAILED DESCRIPTION OF THE DRAWINGS

Figure 1:
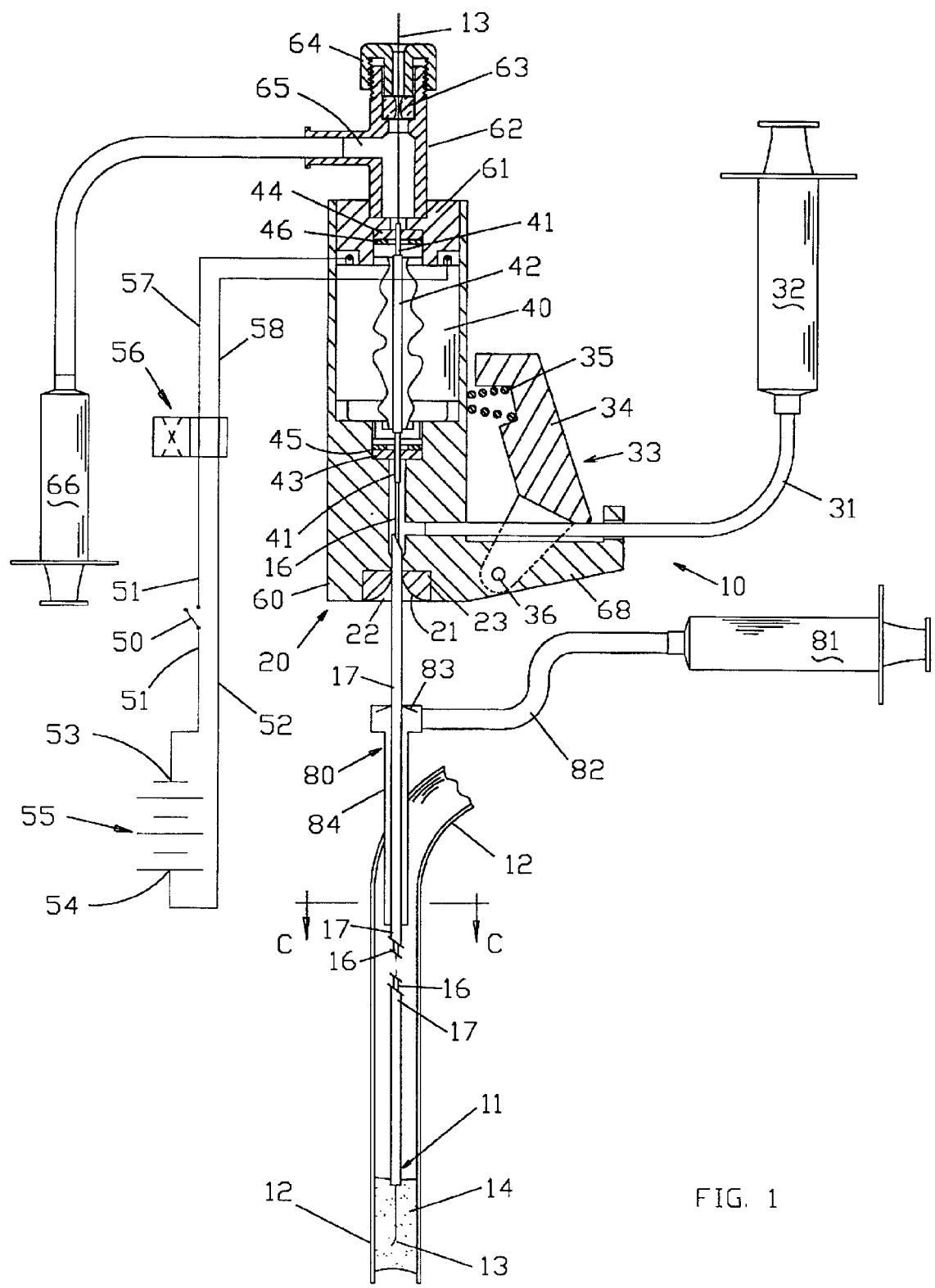
FIG. 1 is a partially sectioned schematic side view of a catheter, embodying the present invention, that inserted into a patient's vasculature through an percutaneous access device.

FIG. 1 shows a flexible catheter 10 having a distal section 11 insertable into a patient's vasculature 12, over a guidewire 13, for removing an obstructive material 14 from the vasculature (the term vasculature refer to the patient's blood vessels; the term "distal" refers to the section or end of the catheter that is inserted into the vasculature whereas the term "proximal" refers to the other section or end of the catheter that remains out of the vasculature, and in general, the terms distal or proximal refer to what is closer to the distal or closer to the proximal ends of the catheter, respectively).

Figure 3:
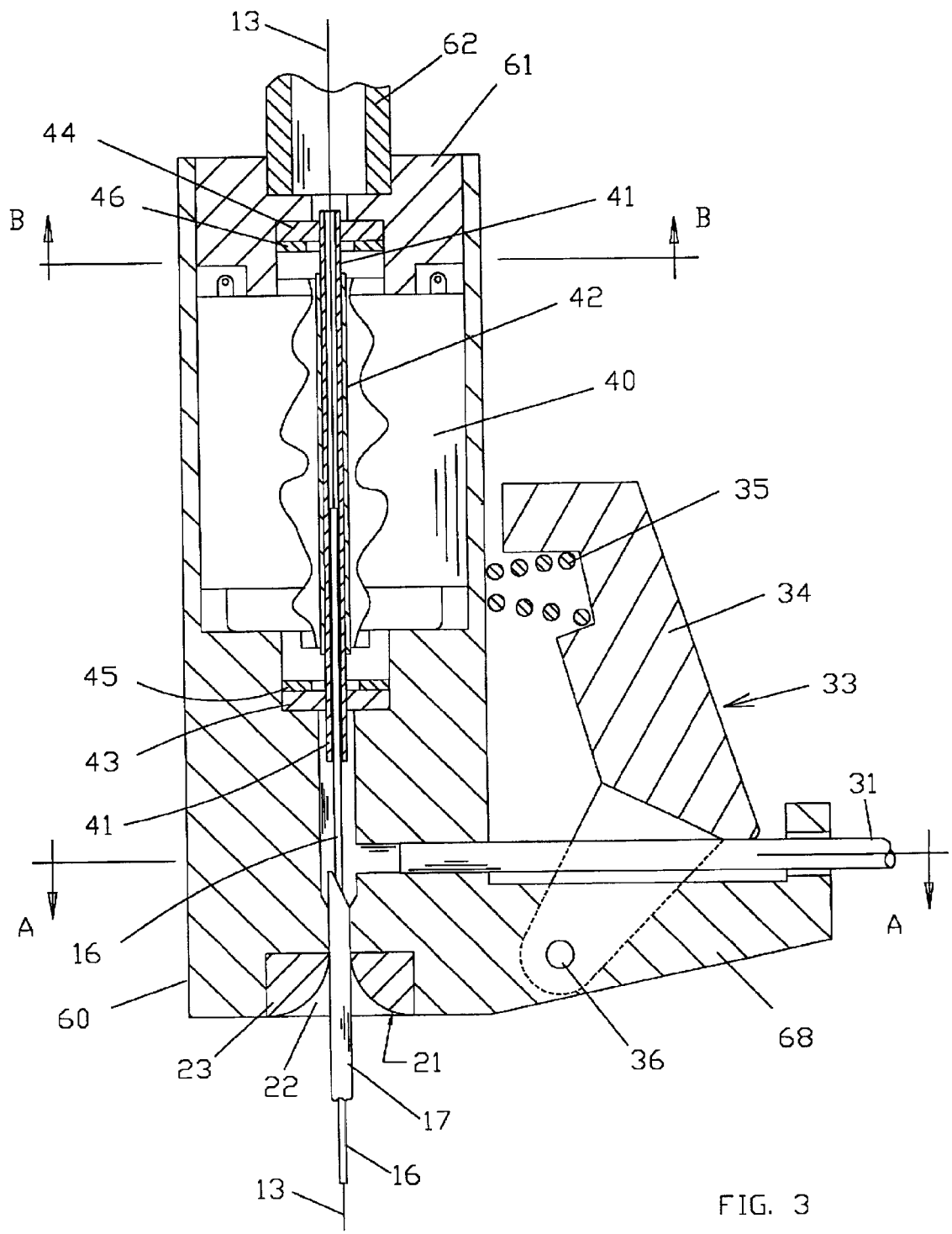
FIG. 3 is a partially sectioned schematic side view of the proximal section of the catheter of FIG. 1 on an enlarged scale.

The catheter 10 comprises a guide wire shield, in the form of an inner tube 16 that is slidable over the guidewire 13. The inner tube is nested in an outer tube 17. Both tubes are flexible, both tubes have smooth inner and outer walls, and both tubes are connected to a proximal base 20 (note also FIG. 3). To prevent the tubes from kinking (diametrically collapsing) at the point that they are connected to the base, their radius of bending is limited by a radius of a wall 21 of a depression 22 defined by the base that surrounds the tubes. Preferably the depression is formed in a separate block 23 that is pressed into the base, after the outer tube 17 has been bonded to the base, to reduce the likelihood of any residue of the bonding process deforming the curvature defined by the radius of the wall 21.

The inner tube can be made with a gradually reduced wall thickness towards the distal end since the torque that the inner tube has to carry is reduced towards the distal end. When the distal end of the catheter is inserted into a tortuous part of the vasculature, such gradually reduced wall thickness increases the overall flexibility of the distal end of the catheter 11 and reduces the frictional forces between the rotating inner tube to the guidewire inside it and the outer tube in which it is nested.

Generally, the wall thickness of the inner tube may range from about 0.001 inch to about 0.005 inch when using harder plastics (e.g., polyimide sold by HV Technologies, Inc., Trenton, Ga.) to twice that range when using softer plastics (e.g., polyethylene, polyurethane or PEBAX sold by Atofina Chemicals, Inc., Phil., Pa.).

The outer tube can also be made of a gradually reduced wall thickness towards the distal end since the longitudinal compression and tension forces that it carries reduce towards the distal end and the reduced wall thickness of the outer tube also increases the overall flexibility of the distal section 11. Generally, the wall thickness of the outer tube may range from about 0.003 inch to about 0.012 inch and to minimize trauma to the vasculature softer plastics and lower Durometers are preferred. Additionally the outer tube can be made from two or more tube sections, bonded, welded or otherwise connected end to end, with the lower Durometer section placed at the distal end.

Figure 2:
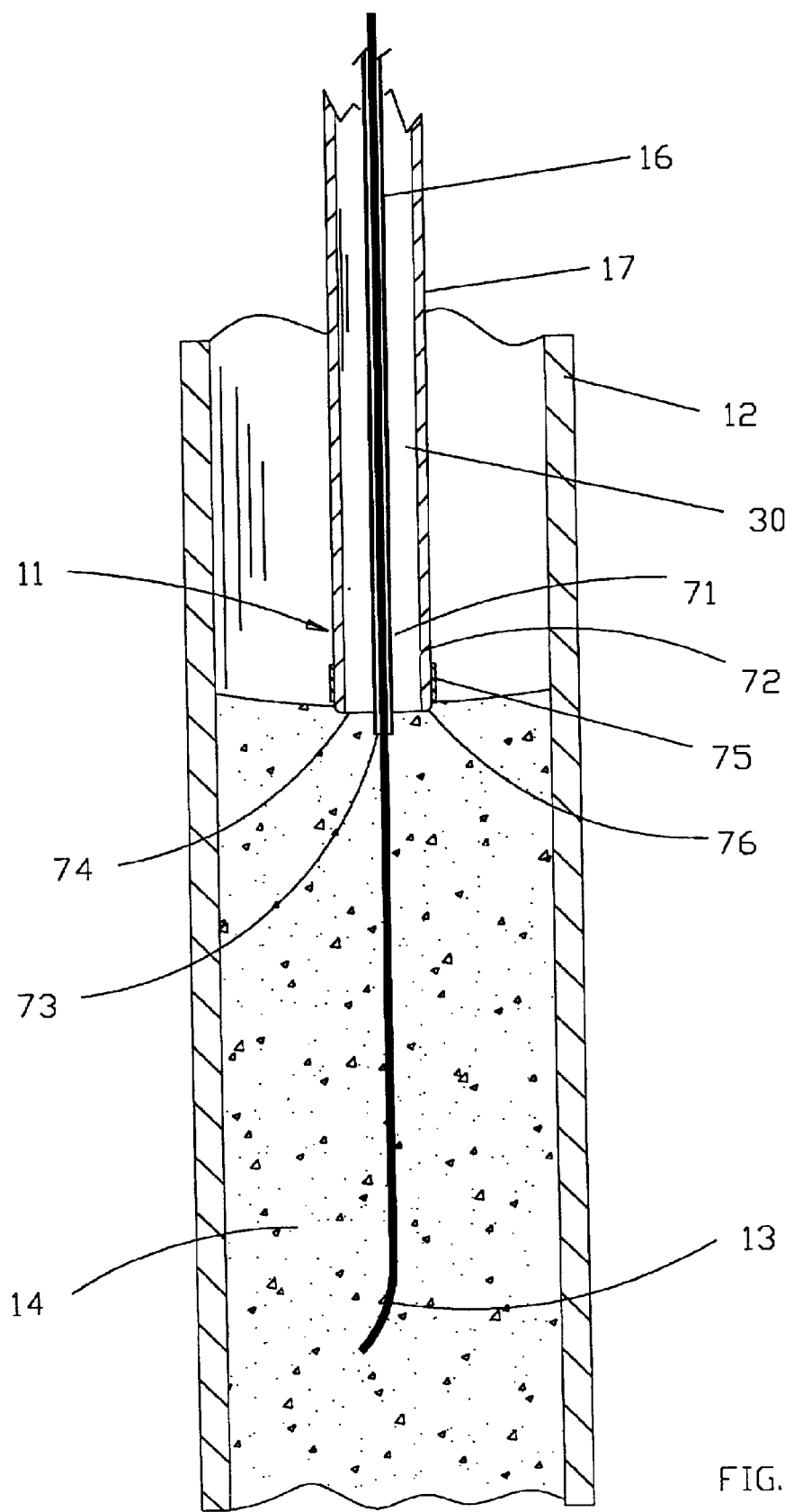
FIG. 2 is a partially sectioned schematic side view of the distal section of the catheter of FIG. 1 on an enlarged scale.
Figure 4:
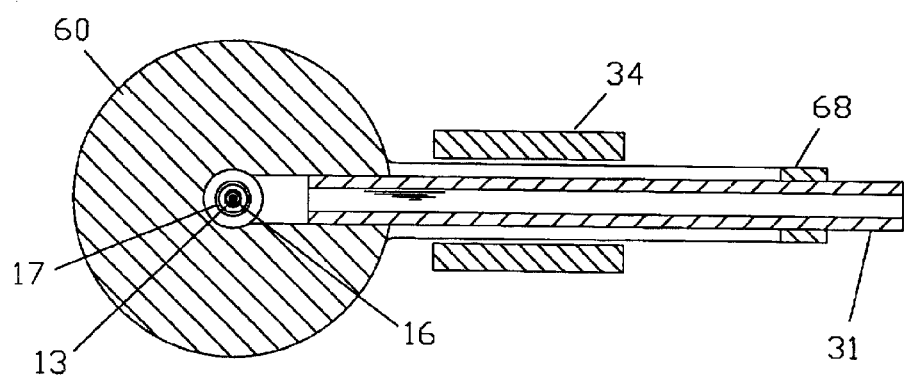
FIG. 4 is a sectional view of the catheter along line A—A marked on FIG. 3.

A void 30, that is unobstructed by mechanical hardware, is defined between the inner wall of the outer tube and the outer wall of the inner tube (note FIG. 2). The void is connected by a first conduit 31 to a first syringe 32 (and as will be understood by those skilled in the art various alternative manual or electric pumping means can be used), which is used to create negative pressure or also to inject fluid through the void into the vasculature. A valve 33 (shown in an open position, note also FIG. 3 and FIG. 4), that is interposed along the conduit selectively opens the first conduit in response to manual force that is applied to a lever 34, overcoming the force of a conical compression spring 35. The spring, which is shown in a compressed position, is interposed between the base 20 and the lever, urging the lever to swivel around a pin 36 clockwise and pinch the first conduit 31 closing flow through it in the absence of the manual force.

Figure 5:
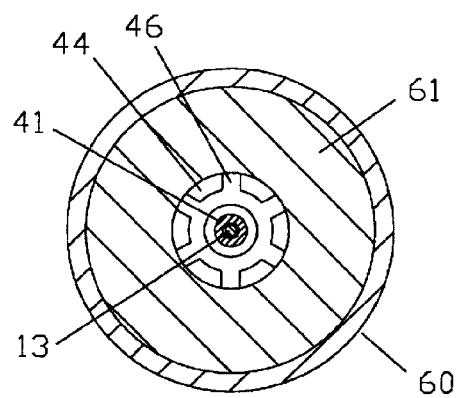
FIG. 5 is a sectional view of the catheter along line B—B marked on FIG. 3.
Figure 6:
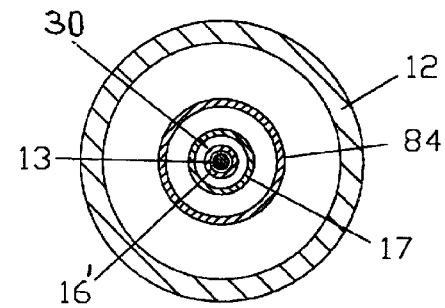
FIG. 6 is a sectional view of the catheter along line C—C marked on FIG. 1.

The inner tube 16 (for example a Polyimide tube with an external diameter of 0.025 inch and an internal diameter of 0.020 inch allowing a nominal 0.006 inch clearance over a guidewire with a diameter of 0.014 inch) passes through and is affixed to a preferably thin walled tube 41 (e.g., a stainless steel tube with an external diameter of 0.039 inch and an internal diameter of 0.027) which in turn passes through and is affixed to a hollow output shaft 42 of an electric motor 40 (the motor is shown with part of its cover removed to expose the shaft 42 which can be made, for example, from a stainless steel tube with an external diameter of 0.080 inch and an internal diameter of 0.040). The thin walled tube 41 extends through seals 43 and 44 that are secured in their respective places by locking rings 45 and 46 (e.g., "TI" series ring made by Rotor Clip Company, Somerset, N.J.; see also FIG. 5). The seals 43 and 44 seal around the tube 41, isolating the motor from fluids. It can be appreciated, by those skilled in the art, that sealing around the 0.039 inch diameter as compared to sealing directly over the 0.080 diameter reduces the frictional torque load on the motor by a factor of about four.

Figure 7:
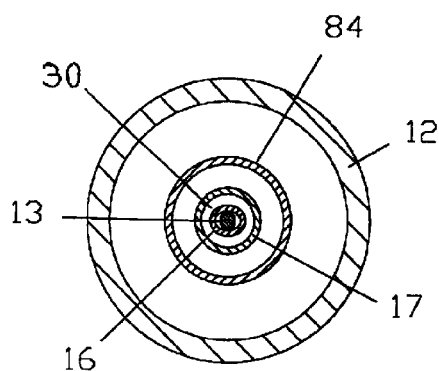
FIG. 7 is same view as FIG. 6 showing a modified embodiment where the inner tube has a non-circular cross section.

Rotation can be used to reduce the frictional resistance to the sliding of the inner tube 16 over the guidewire as the catheter 10 is advanced or withdrawn over it as well as to reduce the frictional resistance to the movement of obstructive material through the void 30 (the effect of relative motion in one direction on the coefficient of fiction in a perpendicular direction is explained in my U.S. Pat. No. 6,143,009 col. 2 lines 58+ which is herein being incorporated by reference). A modified embodiment where the inner tube 16' has, at least along a portion of its length, a non-circular cross section is shown in FIG. 7. As the non-circular tube rotates it makes the suction of material through the void more effective by both reducing the friction as referred to above and agitating the material so that it will not settle in the void and block it.

The motor (40) is activated by a manual switch 50 that connects together two segments of a wire 51. Then wires 51 and 52 connect a negative pole 53 and a positive pole 54 of a battery 55 to an automatic switch 56 that first connects the wire 51 to a wire 57 and the wire 52 to a wire 58 (as schematically shown in solid lines in a box that constitutes the right part of drawing of the switch) and periodically it automatically reverses the connections (as shown schematically in broken lines in a box that constitutes the left part of drawing of the switch) and thereby reverses the polarity of the voltage in wires 57 and 58 and the direction of rotation of the motor. This periodic back and forth reversal of the rotation, reduces friction for the material that longitudinally moves through the void 30 while minimizing buildup of fibers (e.g., fibrin) around the rotating inner tube 16 whereas continuous rotation in one direction tends to draw and wrap-up such fibers into a resilient plug that blocks the void, and if released into the blood stream, is likely to cause additional blockages in the vasculature. As will be understood by those skilled in the art, the electric motor 40 can be replaced with another type of rotary motor (e.g., air or fluid driven motor) that is connected to a suitable power source through appropriate circuitry to achieve the automatic periodic reversal of the direction of rotation as discussed above.

The base 20 comprises a housing 60 that holds together the motor and an adapter 61 to which a proximal portion of a Touhy Borst type fitting 62 is affixed (Touhy Borst type fittings are sold by various companies, e.g., Qosina Corp., Edgewood, N.Y.). The fitting 62 has a seal 63, a screw-on cap 64 to compress the seal, and a side port 65. The compression of the seal against the guidewire 13 can be adjusted by the screw-on cap to establish a tighter seal for minimizing leakage or a looser seal for easier sliding of the guidewire through the seal. The fitting 62 connects the guidewire lumen (the guidewire lumen is the guidewire's continuous path through the catheter that extends through the fitting 62, the tube 41 and the inner tube 16) to a second syringe 66 through the side port 65. A cantilevered extension 68 of the housing supports the lever 34 through the pin 36 and provides a counter-part for the lever against which to pinch the first conduit 31.

The distal section 11 of the catheter 10, shown enlarged in FIG. 2, consists essentially of the distal portions 71 and 72 of the tubes 16 and 17, respectively. The tubes' distal ends 73 and 74 are open and are adjacent to each other. The inner tube preferably slightly protrudes from the outer tube (about 0.06–0.2 inch) to ease loading the guidewire into it, however if a substantial section of the inner tube protrudes from the void it tends to become wrapped with fibers when rotating in the vasculature (rather than inside the void) absent the rapid flow that is induced by negative pressure in the void. The inner tube 16, which rotates intermittently to reduce friction as discussed previously, has no connection to any element for cutting or fragmenting the obstructive material. Thus the obstructive material remains un-fragmented and minimally disturbed until aspirated into the void. This minimizes the danger that a fragment of material would be released into the blood stream and cause a further block in the vasculature.

To assist the physician in locating the distal section of the catheter on standard imaging equipment (e.g., fluoroscope) it is preferably made from a radio-opaque plastic (e.g., plastic containing barium or bismuth compounds) or a thin walled radio opaque ring 75 can be affixed thereto (e.g., a ring containing gold or platinum). The distal end of the outer tube is preferably made from a soft plastic material and its outer corner 76 is preferably rounded to minimize the trauma to the vasculature.

A preferable method for removing an obstructive material from within a patient's vasculature, utilizing the catheter according to the present invention, comprises the following steps:

Introducing a guidewire (the term guidewire as used herein can have additional functions such as light or ultrasound transmission as shown, for example, in my U.S. Pat. No. 4,957,482 issued on Sep. 18, 1990 and U.S. Pat. No. 4,979,939 issued on Dec. 25, 1990, which are herein incorporated by reference) through and into a patient's vasculature and to the vicinity of the obstructive material.

Inserting into the vasculature, over the guidewire, a distal section of the catheter to the vicinity of the obstructive material while preferably rotating the inner tube, as needed, to reduce the frictional resistance between the catheter and the guidewire.

Injecting through the catheter, with the first syringe or another type of injector that is connected to a proximal section of the void, fluid (e.g., saline solution with radio opaque contrast material and Heparin) to assist the physician in visualizing the diseased area of the vasculature on standard imaging equipment (e.g., fluoroscope) and prevent re-cotting of the blood.

Creating negative pressure in the syringe (preferably in the range of about 0.4 to about 1 Bar) and selectively connecting the void to the negative pressure, by activating the valve, to aspirate the obstructive material into the void while preferably rotating the inner tube to reduce the frictional resistance to the movement of obstructive material through the void.

After the void has been used to aspirate the obstructive material it is unadvisable to inject through it into the vasculature (because of the danger of pushing material back into the vasculature). However, small quantities of radio-opaque fluid can be injected with the second syringe through the guidewire lumen to verify flow through vessel that has been cleaned or if the vessel is blocked, such small quantities of radio-opaque fluid assist in the imaging of the disease.

Withdrawing the catheter from the patient's vasculature.

The catheter is preferably introduced into the patient's vasculature through a percutaneous access device 80 (such introducers are sold by, in variety of sizes, from various companies, e.g., Cordis division of Johnson & Johnson) having a tubular section 84 that is designed to be placed in the vasculature and provide access thereto. A hemostatic seal 83 is designed to seal by itself or to seal over the guidewire 13 or over the outer tube 17.

The access device 80 is connected to a third syringe 81 by a third conduit 82 for injecting various fluids (e.g., saline solution with radio opaque contrast material and Heparin to assist visualization and provide a flushing medium to mix with the material as it moves through the void) into the vasculature.

Alternatively, the catheter can be introduced directly into the vasculature, for example when the vasculature is exposed during a surgical procedure.

While a preferred embodiment and method of use of the present invention have been explained above, it should be understood that various changes, adaptations and modifications can be made without departing from the spirit of the invention and the scope of the claims.

What is claimed is:

1. A method for removing an obstructive material from within a patient's vasculature utilizing a flexible catheter slideable over a guidewire that has a rotatable guidewire shield in the form of an inner tube, nested in an outer tube, said tubes having open distal ends, said tubes' distal ends being adjacent to one another, said tubes defining between them an unobstructed void, having an open distal end and a distal section of said catheter consists essentially of the distal portions of said tubes, said inner tube having no connection to any element for cutting or fragmenting said obstructive material so as to minimally disturb the material in the vasculature prior to aspirating it into the void, said method comprising the following steps:

- introducing the guidewire through the patient's vasculature to the vicinity of the obstructive material;
- inserting into said vasculature, over said guidewire, a distal section of the catheter to the vicinity of the obstructive material while selectively rotating the inner tube as needed to reduce the frictional resistance between said catheter and the guidewire;
- connecting said void to negative pressure to aspirate said obstructive material into said void while selectively rotating the inner tube as needed to keep the material moving through said void while minimally disturbing the material in the vasculature; and
- withdrawing the catheter from the patient.

2. A method as in claim 1 with the additional step of injecting radio-opaque fluid through said void into the patient's vasculature prior to connecting said void to negative pressure.

3. A method as in claim 2, further comprising the step of infusing fluid through said inner tube into the patient's vasculature.

4. A method as in claim 1, wherein the catheter is introduced into the patient's vasculature through a percutaneous access device.

* * * * *